United States Patent
Maxwell et al.

(10) Patent No.: US 8,280,679 B2
(45) Date of Patent: Oct. 2, 2012

(54) ACTIVITY MONITOR

(75) Inventors: Douglas James Maxwell, Linlithgow (GB); Nikos Mourselas, Piraeus (GR)

(73) Assignee: Pad Technologies Ltd, Glasgow (GB)

( * ) Notice: Subject to any disclaimer, the term of this patent is extended or adjusted under 35 U.S.C. 154(b) by 462 days.

(21) Appl. No.: 12/303,858

(22) PCT Filed: Jun. 7, 2007

(86) PCT No.: PCT/GB2007/002087
§ 371 (c)(1),
(2), (4) Date: Dec. 8, 2008

(87) PCT Pub. No.: WO2007/141526
PCT Pub. Date: Dec. 13, 2007

(65) Prior Publication Data
US 2010/0228520 A1  Sep. 9, 2010

(30) Foreign Application Priority Data
Jun. 9, 2006 (GB) .................................. 0611442.5

(51) Int. Cl.
*G01C 22/00* (2006.01)
*G06F 17/40* (2006.01)
(52) U.S. Cl. ......... 702/160; 702/176; 702/179; 702/187
(58) Field of Classification Search .......... 702/160–166, 702/176, 179, 187
See application file for complete search history.

(56) References Cited

U.S. PATENT DOCUMENTS

| | | | | |
|---|---|---|---|---|
| 5,485,402 A | * | 1/1996 | Smith et al. | 702/160 |
| 6,611,789 B1 | * | 8/2003 | Darley | 702/160 |
| 2003/0009308 A1 | | 1/2003 | Kirtley | |
| 2005/0096569 A1 | * | 5/2005 | Sato et al. | 600/595 |
| 2006/0195050 A1 | * | 8/2006 | Alwan et al. | 600/595 |
| 2007/0042707 A1 | * | 2/2007 | Better et al. | 455/3.02 |

FOREIGN PATENT DOCUMENTS

| | | |
|---|---|---|
| GB | 2377157 | 1/2003 |
| WO | WO 99/18480 | 4/1999 |
| WO | WO 2004/092744 | 10/2004 |

OTHER PUBLICATIONS

International Search Report for PCT/GB2007/002087, dated Aug. 10, 2007.

* cited by examiner

*Primary Examiner* — Phuong Huynh
(74) *Attorney, Agent, or Firm* — Moore & Van Allen, PLLC; W. Kevin Ransom

(57) ABSTRACT

An activity monitor that has a sensor for sensing movement, a processor for processing sensed data and a memory, wherein the processor is configured to use the sensed data to determine the number of steps taken for each of a plurality of epochs and to determine a measure of the fraction of each epoch spent stepping, the monitor being configured to record in a long term part of the memory at least two of the number of steps; the measure of the fraction of each epoch spent stepping and a measure of cadence calculated using the number of steps and the fraction of each epoch spent stepping.

9 Claims, 3 Drawing Sheets

ACTIVITY MONITOR

FIELD OF THE INVENTION

The present invention relates to an activity monitor. In particular, the present invention relates to a long term activity monitor that is operable to provide a measure of stepping intensity.

BACKGROUND OF THE INVENTION

Physical activity and its measurement have important implications for health and wellbeing. Low levels of physical activity are associated with poor health, such as cardiovascular disease and obesity. Additionally, physical activity measurement gives a quantitative measure of an individual's community mobility. This is important for subjects with an impairment resulting in reduced mobility, for example patients who have had a stroke, or who exhibit behavioural changes, such as bipolar disorder. Stepping is the most important of the primary activities in relation to physical activity. The energy cost of purposeful walking is around four times resting values and the energy expenditure of running can be more than ten times resting values.

Pedometers are the simplest and cheapest devices available for quantifying stepping activity. These provide a cumulative step count that the user can periodically reset. Typically, pedometers are designed to measure purposeful walking and tend to be inaccurate at counting slow steps or fast stepping, e.g. running. Typical pedometers do not measure the intensity of stepping, often referred to as cadence, and provide only a total count of steps taken over a time period and some simple calculations based on this total. There is a range of monitors available which provide a continuous record of the steps taken. Devices that provide this facility include the Actigraph (Actigraph LLC, Florida, USA) and the Stepwatch (CYMA Corporation, Seattle, USA). These record the number of steps taken in a defined period of time, typically one minute.

A problem with devices that record only the number of steps taken is that they cannot accurately reflect the intensity of stepping. For example, if 120 steps were taken in a minute then the cadence is 120 steps per minute. If only 20 steps were taken in the minute then this would be represented as 20 steps per minute. However, if the 20 steps were taken in the minute but only 10 seconds was actually spent stepping then the true cadence would be 20 steps in 10 seconds, which is equivalent to 120 steps per minute. This represents an error in estimating the intensity of the stepping activity of a factor of six and misclassifies a high physical activity period as a low level period.

As well as simple step counters, there are some other, more complex devices available to provide a measure of the variation in stepping intensity over extended periods. For example, the activPAL (PAL Technologies Ltd, Glasgow, UK) and the AMP311 (Dynastream Innovations Inc, Alberta, Canada). These use sophisticated algorithms to detect and record parameters associated with each individual step. This allows a detailed picture of stepping activity to be constructed from the recorded data. Having a detailed record of the pattern of stepping activity is important as the energy cost of a step is not fixed and varies with cadence. Broadly, the energy cost of walking a mile is the same as running a mile, i.e. the energy cost per unit of distance traveled is similar. However, as stepping rate increases stride length also increases. Hence, at higher stepping rates each unit of distance is covered in less time and the physical effort, i.e. the energy cost, of the stepping activity is increased.

Whilst some of the more complex devices provide useful information, a problem with these is that they do not provide a measure of true cadence and the power requirements are high. This is because they need a relatively large on-board memory and processing capability. This means that these devices are either unsuitable for long term use, or would have to be made relatively large to accommodate a big enough battery. Neither of these scenarios is ideal where the monitors are to be used by patients who have long-term mobility problems and where information on their levels of activity could provide valuable information. For example, lower limb amputees use a prosthetic leg and they typically undergo an annual assessment. This leg is a medical device and its performance is governed by international standards. By monitoring prosthetic leg function and use over the extended period between clinic appointments, valuable information on device performance and patient wellbeing can be generated. However, current devices are not suitable for this type of use, and so there is currently no opportunity to obtain such valuable information over extended periods.

SUMMARY OF THE INVENTION

According to the present invention, there is provided an activity monitor that has a sensor for sensing movement and a memory, the monitor being configured to record in a long term part of the memory at least two of the number of steps taken per defined time period, a measure of the fraction of the defined time period actually spent stepping and a measure of the true cadence determined using the number of steps and the measure of the fraction of the defined time period actually spent stepping.

Preferably, only two of the number of steps taken per defined time period, the measure of the fraction of the defined time period actually spent stepping and the true cadence are stored. Preferably, a flag is also set to indicate the dominant device orientation over the epoch (ie vertical or horizontal).

By saving only a limited amount of information for each defined time period, sometime referred to as epoch, the amount of physical memory required to provide a true measure of the cadence is minimised and power consumption can be reduced, whilst allowing the true cadence per epoch to be calculated. This is advantageous, because in use the activity monitor will have to be used over extended periods, for example a year. For these extended recording periods power-consumption is a limiting factor. Minimising the size of the memory and the battery needed, allows the overall size of the monitor to be reduced. This is important, because for subject compliance the monitor has to be as small and easy to apply as possible.

In practice, the dimensions and weight of the device are minimised by using an energy efficient design, which maximises the activity information recorded against minimal power consumption. This results in a long life monitor that is small and compact. In fact, this monitor can be made small enough to fit inside the shin of a prosthetic leg, whilst having a recording capacity in excess of one year.

According to another aspect of the present invention, there is provided a method for measuring activity comprising sensing movement using a sensor; storing sensed movement data; using the sensed data to determine the number of steps taken for each of a plurality of epochs, as well as measure of the fraction of each epoch spent stepping, and using the number of steps taken and the measure of the fraction of each epoch spent stepping to determine a measure of the cadence for each epoch. Preferably, the cadence is determined by dividing the number of steps by the fraction of each epoch spent stepping.

BRIEF DESCRIPTION OF THE DRAWINGS

Various aspects of the invention will now be described by way of example only and with reference to the accompanying drawings, of which.

SPECIFIC DESCRIPTION OF THE DRAWINGS

Figure 1:
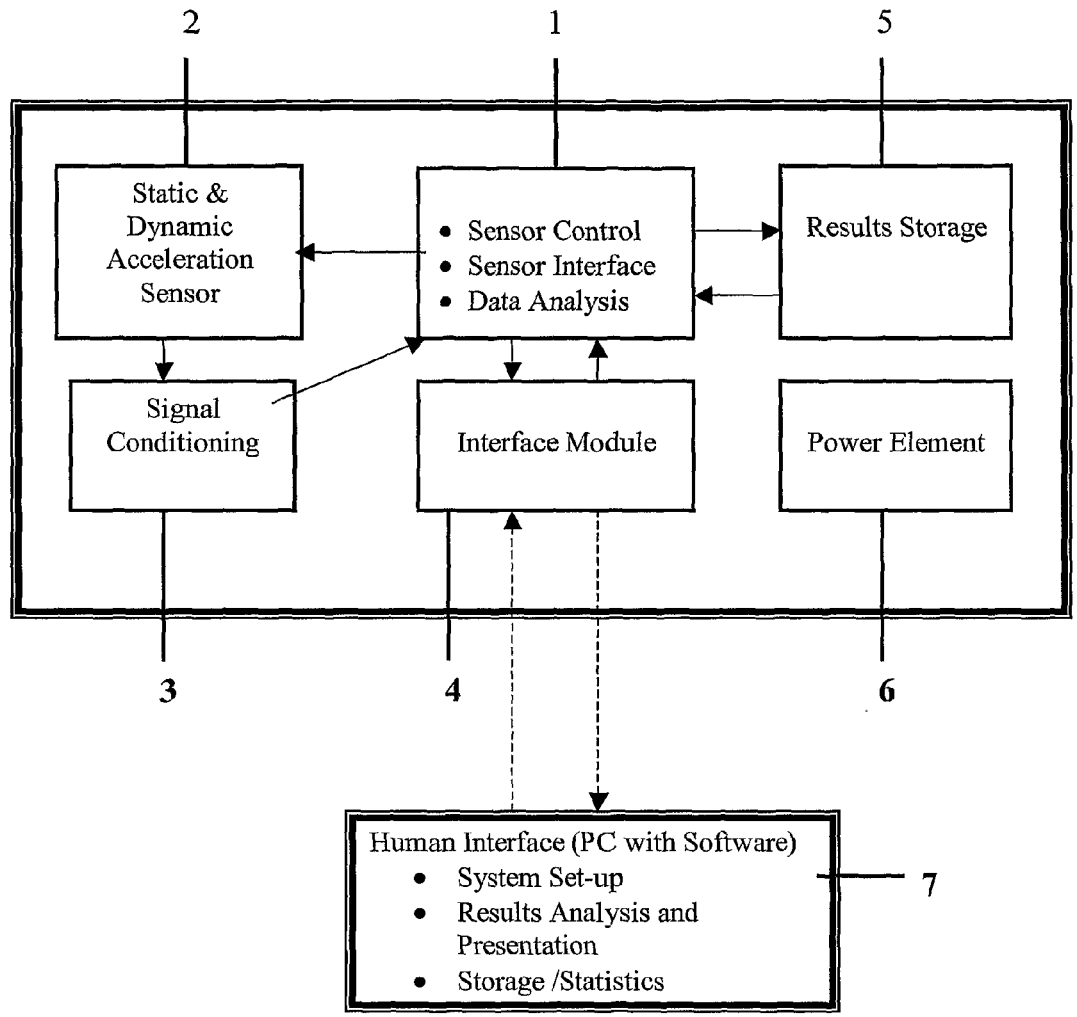
FIG. 1 is a block diagram of a long-term activity monitor.

FIG. 1 shows a long-term activity monitor. This is a body worn sensing and recording device consisting of a control module 1 that is connected to each of an acceleration sensor 2; a signal conditioning module 3; an interface module 4 and a memory 5. Supplying all of these is a power element 6. The interface module 4 provides a connection to an external human interface 7, thereby to allow communication with the control module 1, so that the contents of the memory 5 can be accessed. This provides a means for accepting user instructions, for example for set-up, and/or to transfer the stored data to another location. Typically, the human interface module 7 is a software module residing at a personal computer. This allows programming and testing of the device before use and/or the presentation of activity monitoring results.

The acceleration sensor 2 is operable to detect both static and dynamic accelerations. This means that it can provide information on both the long-term position of the structure on which it is fixed relative to gravity, for example horizontal and vertical, and the movement of this structure. The sensor output is passed to the conditioning module 3, where it is filtered and amplified. Any suitable filter may be used in the conditioning module 3. However in a preferred example, an anti-aliasing low pass filter in the range of 5-40 Hz is used to screen out high frequencies not associated with human movement.

The output of the conditioning module 3 is connected to the control module 1, which is the main unit of the system, and includes a processor. The main task of the control module is to implement algorithms for identification of position and movement changes in the incoming digital signal from the conditioning module. Included in the processor is a buffer memory for the temporary storage of data that is being processed. Data that is to be stored long term is saved in the memory 5.

The control module 1 accepts the analogue signal from the conditioning module 3 and converts this to a digital signal, typically using a 10 Hz sampling rate. User-defined thresholds are used for position measurement and movement (step) detection. To do this, a low pass filter is applied to the digital signal and the filtered signal is classified against the programmed thresholds for position allowing the orientation of the device with respect to gravity to be determined. If the device is judged to be in an appropriate orientation for stepping activity to occur (upright) then the unfiltered signal is tested for the presence of stepping movements. Algorithms are then applied to extract position and movement from the data signal over a defined time period or epoch, typically one minute, thereby to provide stepping information.

Stepping is detected using temporal criteria. Stepping movements are characterised as a series of peaks and troughs in the signal from the sensor. The step detection algorithm determines if a true stepping event has occurred by examining the interval since the last stepping event and the magnitude of the signal at the peak event. User-defined thresholds are applied for maximum and minimum inter-step interval and peak magnitude. In this way steps as a function of time can be determined for each epoch. This information is then processed to determine the total number of steps taken and the time between such steps. Then the sum of the inter-step intervals is calculated. Once this is done, the number of steps identified per epoch is recorded in the memory 5, together with the sum of the inter-step intervals for the epoch. Alternatively or additionally, the recorded data may include a measure of the true cadence determined using the number of steps and the measure of the fraction of the epoch actually spent stepping. These three values are the only quantitative stepping values stored in the long-term memory, and in practice it is preferred that only two of these are stored, thereby keeping memory requirements to a minimum. Preferably, a flag is also set in the memory 5 to indicate the dominant device orientation over the epoch (ie vertical or horizontal). All the sensed data is then either deleted from the buffer or overwritten by data for the next epoch.

The power module 6 provides the power to all other modules of the device. It is managed by the control module 1 to minimise power drain to peripheral modules. Power consumption is directly related to the recording period. Sensing and memory writing are the two highest power requirements. By storing the inter-step intervals for each epoch rather than all the stepping data captured, information can be conveyed as to whether for example ten fast steps were taken in an otherwise static minute, or ten very slow steps were uniformly taken inside that minute. Doing this reduces the memory requirements for the long-term memory 5 and so reduces the overall power requirements for the device. By using a relatively low sampling frequency on the sensor signal (typically 10 Hz) and an epoch of one minute, information content is maximised while further reducing power consumption. With these settings, a single 2000 mAh battery will provide in excess of one year's recording capability.

Figure 2:
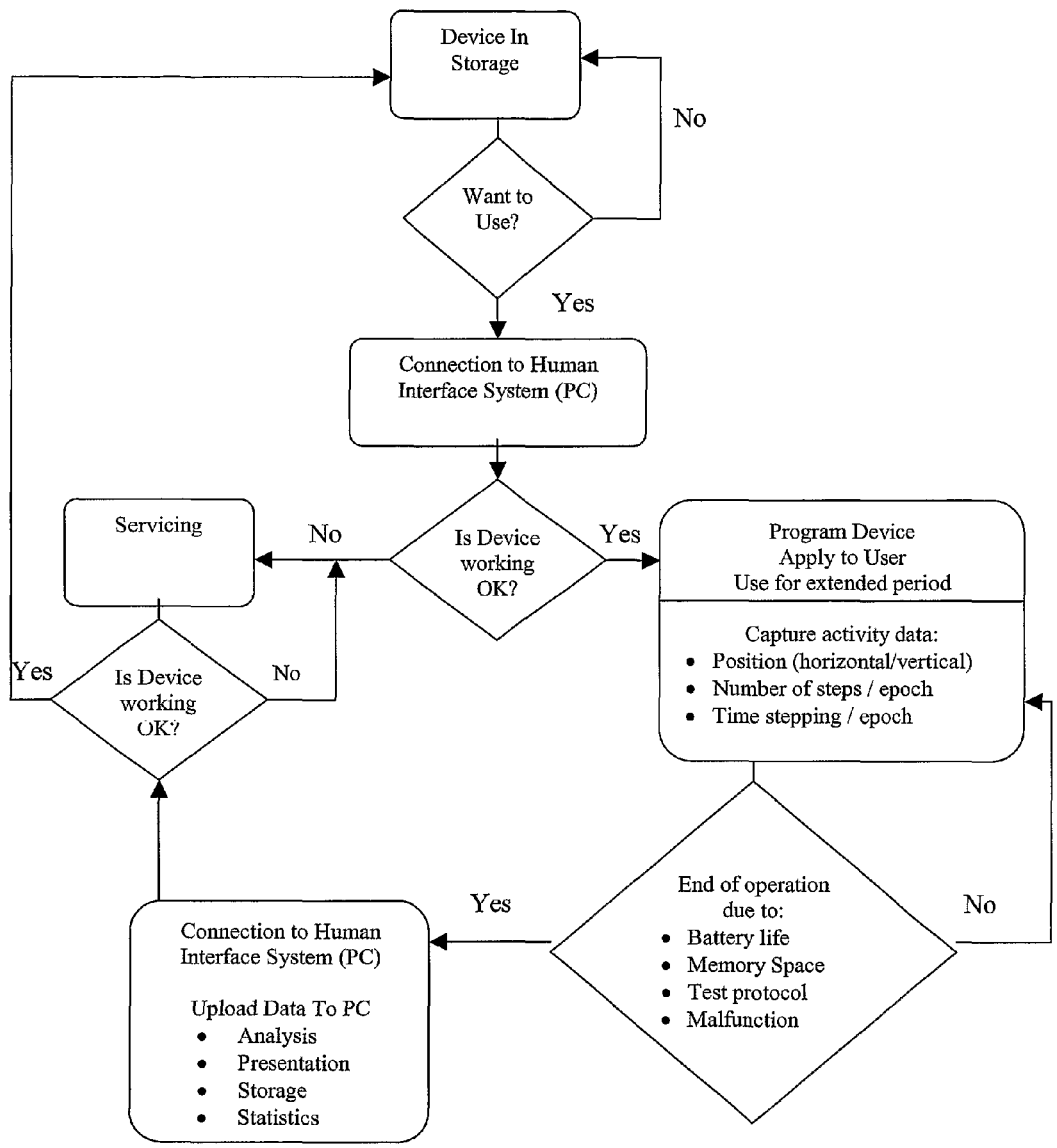
FIG. 2 is a flow diagram of the steps taken by the activity monitor in use.

FIG. 2 shows a flowchart of a typical application procedure, where the device is being drawn from stock, tested, programmed and fitted to an individual for a period of up to 18 months and then returned and inquired at the host station. When the device is selected for use, it is firstly connected to an interface with, for example, a PC for testing. In the event that it is working, it can be programmed and applied to a user for extended use. Where the user has a prosthetic leg, the device is typically fitted to the shin of the leg so that it can be used to continuously monitor the patient's activity levels over an extended period of time by capturing data on position, i.e. horizontal or vertical, the numbers of steps per epoch and the time spent stepping during each epoch. This data capturing and monitoring is done continuously until, for example, the battery runs out or the memory is full or a predetermined test time has elapsed or the device has malfunctioned. In any of these cases, at the end of the operation, the data captured by the device is up-loaded via the interface to a PC for analysis and/or presentation. In this way, there is provided a simple and effective way for capturing important long term clinical data.

Figure 3:
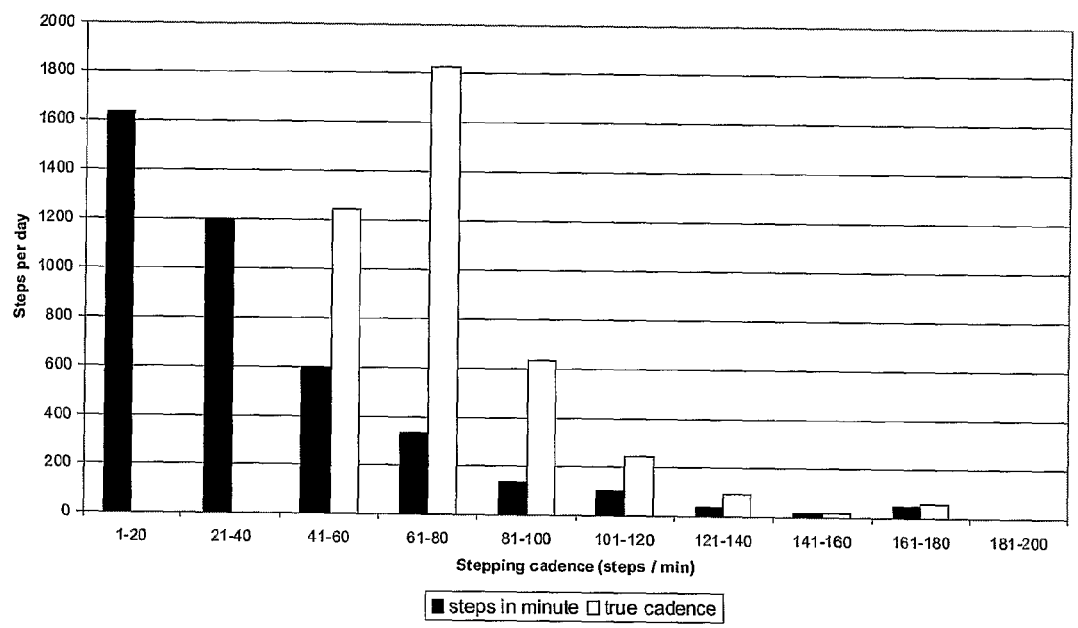
FIG. 3 is a histogram showing the difference between the steps in a minute and true cadence.

The activity monitor of the present invention provides significantly enhanced mobility information. The data that can be derived provides an improved indication of a user's activity levels over what could be obtained with a simple step counter. In particular, the device of the present invention allows the true pace of stepping in each epoch to be determined and recorded in such a manner that long-term use becomes a practical possibility. In contrast to known approaches which simply count the number of steps in each epoch and express intensity as steps taken per epoch, the activity monitor in which the present invention is embodied is able to generate an accurate intensity for each epoch by recording both the number of steps taken in each epoch and the time spent stepping. By dividing the number of steps taken by the time spent stepping the intensity of the stepping activity can be expressed in steps per minute. This gives a measure of the true cadence, as shown in FIG. 3, which represents an accurate measure of the actual intensity of stepping. For example if a subject takes 60 steps in 30 seconds current approaches would describe this at 60 steps per minute however the true cadence is 60 steps in 30 seconds or 120 steps per minute. By using the simple and effective design of the present invention, this enhanced information can be provided even within the constraints of a very low power, long life device.

The above-described system can be applied to able-bodied subjects or those with prosthetic limbs. Typically the device is worn on the lower leg, but thigh and trunk placements are alternatives.

A skilled person will appreciate that variations of the disclosed arrangements are possible without departing from the invention. For example, although the interface 4 is shown as a separate module, its functions may be integrated into the control unit 1. In addition, a USB communications module can be included to provide direct USB connection to the host. Also, whilst in the monitor described the fraction of stepping step is recorded, instead the fraction of time spent not stepping could be recorded and used later to determine the fraction of time spent stepping. Accordingly, the above description of a specific embodiment is made by way of example only and not for the purposes of limitations. It will be clear to the skilled person that minor modifications may be made without significant changes to the operation described.

The invention claimed is:

1. An activity monitor comprising:
    a sensor for sensing movement;
    a processor for processing sensed data; and
    a memory,
    wherein the processor is configured to use the sensed data to determine the number of steps taken for each of a plurality of defined time periods and to determine a measure of the fraction of each defined time period spent stepping,
    the activity monitor being configured to record in the memory two or more of the following:
    the number of steps,
    the measure of the fraction of each defined time period spent stepping, and
    a measure of cadence calculated using the number of steps and the fraction of each defined time period spent stepping.

2. An activity monitor as claimed in claim 1 wherein only one of the measure of the fraction of each defined time period spent stepping and cadence is recorded.

3. An activity monitor as claimed in claim 1 wherein data that is sensed is stored in a short term or buffer part of the memory.

4. An activity monitor as claimed in claim 2, wherein the short term or buffer is within an on-board processor.

5. An activity monitor as claimed in claim 2 wherein the sensed data is deleted or overwritten once the number of steps and stepping fraction per defined time period are determined.

6. An activity monitor as claimed in claim 1 that is configured to store an indication of a dominant device orientation for each defined time period.

7. An activity monitor as claimed in claim 6 wherein a flag is provided which in one state is indicative that the dominant device orientation was horizontal and in the other state is indicative that the dominant device orientation was vertical.

8. A method for measuring activity comprising:
    sensing movement using a sensor;
    storing sensed movement data;
    using the sensed data to determine the number of steps taken for each of a plurality of defined time periods, as well as measure of the fraction of each defined time period spent stepping; and
    using the number of steps taken and the measure of the fraction of each defined time period spent stepping to determine a measure of cadence for each defined time period.

9. A method as claimed in claim 8 wherein the cadence is determined by dividing the number of steps by the fraction of each defined time period spent stepping.

* * * * *

UNITED STATES PATENT AND TRADEMARK OFFICE
CERTIFICATE OF CORRECTION

PATENT NO. : 8,280,679 B2  
APPLICATION NO. : 12/303858  
DATED : October 2, 2012  
INVENTOR(S) : Douglas James Maxwell et al.

Page 1 of 1

It is certified that error appears in the above-identified patent and that said Letters Patent is hereby corrected as shown below:

Title Page, Item (73) Assignee should read as follows:

--Pal Technologies Ltd--

Signed and Sealed this  
Thirtieth Day of April, 2013

Teresa Stanek Rea  
*Acting Director of the United States Patent and Trademark Office*